(12) United States Patent
Zhang et al.

(10) Patent No.: US 10,702,400 B2
(45) Date of Patent: Jul. 7, 2020

(54) MECHANICAL EXOSKELETON WEARABLE APPARATUS, OPERATION CONTROL METHOD AND OPERATION CONTROL DEVICE FOR THE SAME

(71) Applicant: BOE Technology Group Co., Ltd., Beijing (CN)

(72) Inventors: Yifei Zhang, Beijing (CN); Kai Zhao, Beijing (CN); Ying Zhang, Beijing (CN); Yu Gu, Beijing (CN); Hongli Ding, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 251 days.

(21) Appl. No.: 15/647,364

(22) Filed: Jul. 12, 2017

(65) Prior Publication Data
US 2018/0036146 A1 Feb. 8, 2018

(30) Foreign Application Priority Data

Aug. 3, 2016 (CN) .......................... 2016 1 0626933

(51) Int. Cl.
*B25J 9/00* (2006.01)
*A61F 2/68* (2006.01)
(Continued)

(52) U.S. Cl.
CPC .................. *A61F 2/60* (2013.01); *A61F 2/68* (2013.01); *A61F 5/0102* (2013.01); *A61H 3/00* (2013.01);
(Continued)

(58) Field of Classification Search
CPC .... A61F 2/68; A61F 2/60; A61F 2/604; A61F 2/64; A61F 2/66; A61F 5/0123;
(Continued)

(56) References Cited

U.S. PATENT DOCUMENTS 7,549,969 B2 * 6/2009 van den Bogert .... A61F 5/0102
602/16
2009/0017990 A1 1/2009 Ochi et al.

FOREIGN PATENT DOCUMENTS

CN 1586434 A 3/2005
CN 1943531 A 4/2007
(Continued)

OTHER PUBLICATIONS

First Office Action, including Search Report, for Chinese Patent Application No. 201610626933.0, dated Dec. 22, 2017, 12 pages.

*Primary Examiner* — Brian A Dukert
(74) *Attorney, Agent, or Firm* — Westman, Champlin & Koehler, P.A.

(57) ABSTRACT

A mechanical exoskeleton wearable apparatus and an operation control method as well as an operation control device for the same are provided in the embodiments of the disclosure, so as to enrich usable functionalities of the mechanical exoskeleton wearable apparatus. The mechanical exoskeleton wearable apparatus includes a foot wearable mechanism; a leg wearable mechanism including: shank supports articulated with the foot wearable mechanism, thigh supports articulated with the shank supports, and first stroke regulators articulated with the foot wearable mechanism and the thigh supports respectively at both ends; and a hip support mechanism configured to connect with the thigh supports. Each of the first stroke regulators is configured to be extendable and retractable with a leg action of a user, and an extending or retracting condition thereof is lockable.

19 Claims, 6 Drawing Sheets

(51) Int. Cl.
  *A61F 2/60* (2006.01)
  *A61H 3/00* (2006.01)
  *A61F 5/01* (2006.01)
(52) U.S. Cl.
  CPC ..... *B25J 9/0006* (2013.01); *A61F 2005/0158* (2013.01); *A61H 2201/165* (2013.01); *A61H 2201/1642* (2013.01); *A61H 2201/1666* (2013.01)
(58) Field of Classification Search
  CPC ..... A61F 5/0127; A61F 5/0102; B25J 9/0006; A61H 3/00
  See application file for complete search history.

(56) References Cited

FOREIGN PATENT DOCUMENTS

| | | |
|---|---|---|
| CN | 104000708 A | 8/2014 |
| CN | 104473486 A | 4/2015 |
| CN | 204743334 U | 11/2015 |
| CN | 105411813 A | 3/2016 |
| CN | 205835312 U | 12/2016 |
| WO | 2006/113520 A3 | 10/2006 |
| WO | 2015/136214 A1 | 9/2015 |
| WO | 2015/195310 A3 | 12/2015 |

\* cited by examiner

MECHANICAL EXOSKELETON WEARABLE APPARATUS, OPERATION CONTROL METHOD AND OPERATION CONTROL DEVICE FOR THE SAME

CROSS-REFERENCE TO RELATED INVENTION

The present disclosure claims the benefit of Chinese Patent Application Invention No. 201610626933.0 filed on Aug. 3, 2016 in the State Intellectual Property Office of China, the whole disclosure of which is incorporated herein by reference.

BACKGROUND OF THE INVENTION

Field of the Invention

Embodiments of the present disclosure relate to the technical field of a wearable apparatus, and in particular, to a mechanical exoskeleton wearable apparatus, an operation control method and an operation control device for the same.

Description of the Related Art

An mechanical exoskeleton wearable apparatus which is also known as "exoskeleton armour" or "exoskeleton mecha", which is similar to an exoskeleton of an insect in structure thereof and is wearable on human body for providing additional power and protection so as to enhance functions of human body. With a dedicatedly designed mechanical exoskeleton, people may run even faster, jump even higher or carry even heavier weights as compared with ordinary people.

Nowadays, the mechanical exoskeleton is not powerful enough in its functionality; therefore, it is a technical problem required to be solved how to enrich usable functionalities thereof.

SUMMARY OF THE INVENTION

The embodiments of the present disclosure have been made to overcome or alleviate at least one aspect of the above mentioned disadvantages and/or shortcomings in the prior art, by providing a mechanical exoskeleton wearable apparatus, an operation control method and an operation control device for the same to enrich usable functionalities of the mechanical exoskeleton wearable apparatus.

Following technical solutions are adopted in exemplary embodiments of the invention for achieving the above desired technical purposes.

According to an aspect of the exemplary embodiment of the present disclosure, there is provided a mechanical exoskeleton wearable apparatus, comprising: a foot wearable mechanism; a leg wearable mechanism comprising: shank supports articulated with the foot wearable mechanism, thigh supports articulated with the shank supports, and first stroke regulators articulated with the foot wearable mechanism and the thigh supports respectively at both ends; and a hip support mechanism configured to connect with the thigh supports; each of the first stroke regulator is configured to be extendable and retractable with a leg action of a user who wears the mechanical exoskeleton wearable apparatus, and an extending or retracting condition thereof is lockable.

According to another aspect of the exemplary embodiment of the present disclosure, there is provided an operation control method for a mechanical exoskeleton wearable apparatus, comprising: acquiring an extending or retraction stroke of a first stroke regulator; and controlling the first stroke regulator to be locked at an extending or retracting condition thereof once the extending or retraction stroke thereof reaches a predetermined extending or retraction stroke threshold.

According to yet another aspect of the exemplary embodiment of the present disclosure, there is provided an operation control device for a mechanical exoskeleton wearable apparatus, comprising: an acquisition unit configured to acquire an extending or retraction stroke of a first stroke regulator; and a control unit configured to control the first stroke regulator to be locked at an extending or retracting condition thereof once the extending or retraction stroke thereof reaches a predetermined extending or retraction stroke threshold

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

DETAILED DESCRIPTION OF PREFERRED EMBODIMENTS OF THE INVENTION

Exemplary embodiments of the present disclosure will be described hereinafter in detail with reference to the attached drawings, wherein the like reference numerals refer to the like elements. The present disclosure may, however, be embodied in many different forms, and thus the detailed description of the embodiment of the disclosure in view of attached drawings should not be construed as being limited to the embodiment set forth herein; rather, these embodiments are provided so that the present disclosure will be thorough and complete, and will fully convey the general concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Respective dimension and shape of each component in the drawings are only intended to exemplarily illustrate the contents of the disclosure, rather than to demonstrate the practical dimension or proportion of components of the mechanical exoskeleton wearable apparatus and an operation control device therefor.

According to a general technical concept of the present disclosure, in order to enrich usable functionalities of the mechanical exoskeleton wearable apparatus, there is provided a mechanical exoskeleton wearable apparatus, and an operation control method as well as an operation control device therefor. In order to illustrate the purposes, technical solutions and technical advantages of the disclosure more clearly, embodiments thereof are exemplified hereinafter so as to provide a more comprehensive depiction of the disclosure in details.

Figure 1:
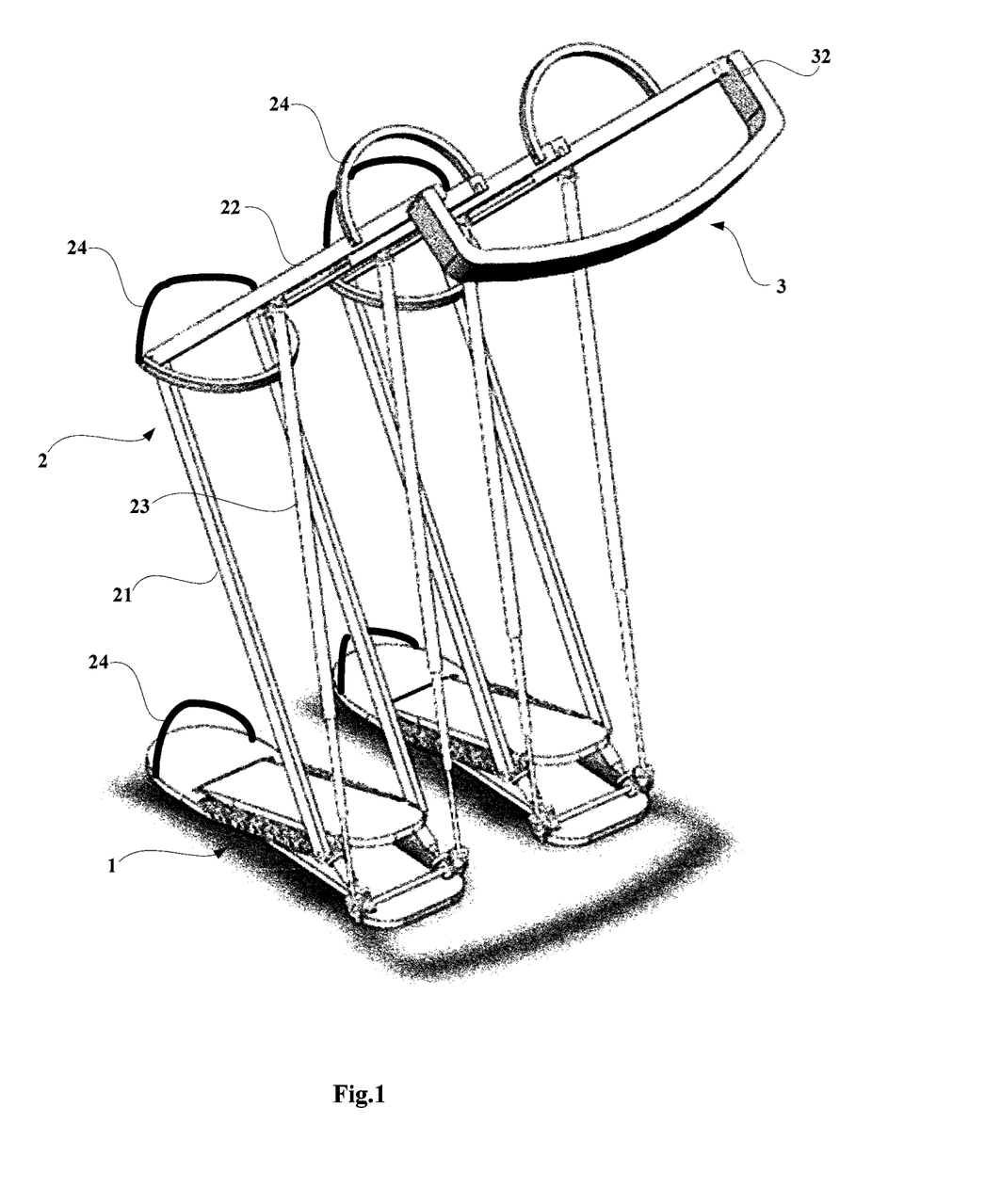
FIG. 1 illustrates a schematic view of a mechanical exoskeleton wearable apparatus according to an exemplary embodiment of the disclosure.

As illustrated in FIG. 1, a mechanical exoskeleton wearable apparatus is provided in an exemplary embodiment of the disclosure, comprising a foot wearable mechanism 1, a leg wearable mechanism 2 and a hip support mechanism 3. The leg wearable mechanism 2 comprises: shank supports 21 articulated with the foot wearable mechanism 1, thigh supports 22 articulated with the shank supports 21, and first stroke regulators 23 articulated with the foot wearable mechanism 1 and the thigh supports 22 respectively at both ends; and the first stroke regulators 23 are configured to be extendable and retractable with a leg action of a user who wears the mechanical exoskeleton wearable apparatus, and an extending or retracting condition thereof may be lockable. And the hip support mechanism 3 is configured to connect with the thigh supports 22.

By way of example, a body of the mechanical exoskeleton wearable apparatus is formed by a material which is provided with a relative lower density but a relative larger strength as compared with a conventional metallic limb prosthesis adopted in a surgical operation, so as to facilitate decreasing wearing load for human body and providing sufficient rigidity therefor, for example the material including but not limited to titanium or titanium alloy metals. A specific way for fixing the mechanical exoskeleton wearable apparatus onto the human body is not restricted; as illustrated in FIG. 1, in an illustrative embodiment, each of the foot wearable mechanism 1 and the leg wearable mechanism 2 is provided with a binding band or binding bands 24, respectively. The binding band(s) may not be restricted in quantity thereof; and the specific number thereof may be determined so as to ensure a secured fix between the mechanical exoskeleton wearable apparatus and the human body. And the hip support mechanism may not be restricted in its shape; by way of example, the hip support mechanism may be designed to be in a form of U-shape so as to conform to a specific shape of a hip of the human body and thus to provide a sufficiently comfortable support.

In a case that the user wears the mechanical exoskeleton wearable apparatus provided by an embodiment of the disclosure, when a user runs or walks, the foot wearable mechanism 1, the shank supports 21 and the thigh supports 22 may follow an action of the human body of the user while the first stroke regulators 23 may also extend/stretch or retract with an action of the leg of the human body. Therefore, the user may walk or run freely, without being impeded or obstructed by the mechanical exoskeleton wearable apparatus, and the mechanical exoskeleton wearable apparatus may keep a perfect fit with the foot, the shank and the thigh of the user in a follow-up process during which it simulates a walking/running action of the user.

Furthermore, by way of example, the user may implement a seat functionality of the mechanical exoskeleton wearable apparatus by locking the first stroke regulators 23 at the extending or retracting condition thereof. Specifically, when the first stroke regulators 23 is locked at its extending or retracting condition, an angle between one of the shank supports 21 and a corresponding one of the thigh supports 22 are fixed, e.g., a fixed angle larger than 90 degrees and smaller than 180 degrees so as to form a secured support therebetween, such that the user may sit safely on the hip support mechanism 3.

Above design schemes of embodiments of the disclosure enrich usable functionalities of the mechanical exoskeleton wearable apparatus, such that the mechanical exoskeleton wearable apparatus is more applicable practically.

The first stroke regulators 23 may not be restricted in specific structural form thereof. For example, in an optional embodiment of the disclosure, each of the first stroke regulators is an electric cylinder provided with a switch. When the electric cylinder is switched on, the corresponding first stroke regulator may extend/stretch or retract with the action of the leg of the human body; and when the electric cylinder is switched off, the corresponding first stroke regulator may be locked at its extending or retracting condition of the switch-off moment of the electric cylinder.

Figure 2:
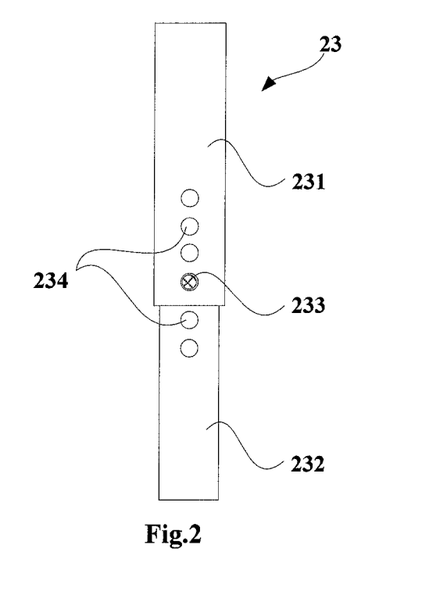
FIG. 2 illustrates a schematic view of a first stroke regulator according to an exemplary embodiment of the disclosure.

As illustrated in FIG. 2, in another optional embodiment of the disclosure, each of the first stroke regulators comprises a first adjustment rod 231, a second adjustment rod 232, and a lock-pin 233. The first adjustment rod 231 and the second adjustment rod 232 are assembled slidably relative to each other and provided respectively with a plurality of pinholes 234 arranged in a relative sliding direction. Once the lock-pin 233 is not inserted into a pair of respective pinholes of the first adjustment rod 231 and the second adjustment rod 232 disposed to be aligned with each other, the corresponding first stroke regulator 23 is capable of extend or retract with the action of the leg of the human body; and once the lock-pin is inserted into a pair of respective pinholes of the first adjustment rod and the second adjustment rod disposed to be aligned with each other, the extending or retracting condition of the corresponding first stroke regulator 23 is locked.

By the technical solutions of above two embodiments, the user may operate manually the first stroke regulators 23. When the extending or retracting condition of one of the first stroke regulators 23 is locked by switching off the electric cylinder or by inserting the lock-pin into a pair of respective pinholes of the first adjustment rod and the second adjustment rod disposed to be aligned with each other, the seat functionality of the mechanical exoskeleton wearable apparatus may be utilized safely.

Figure 3:
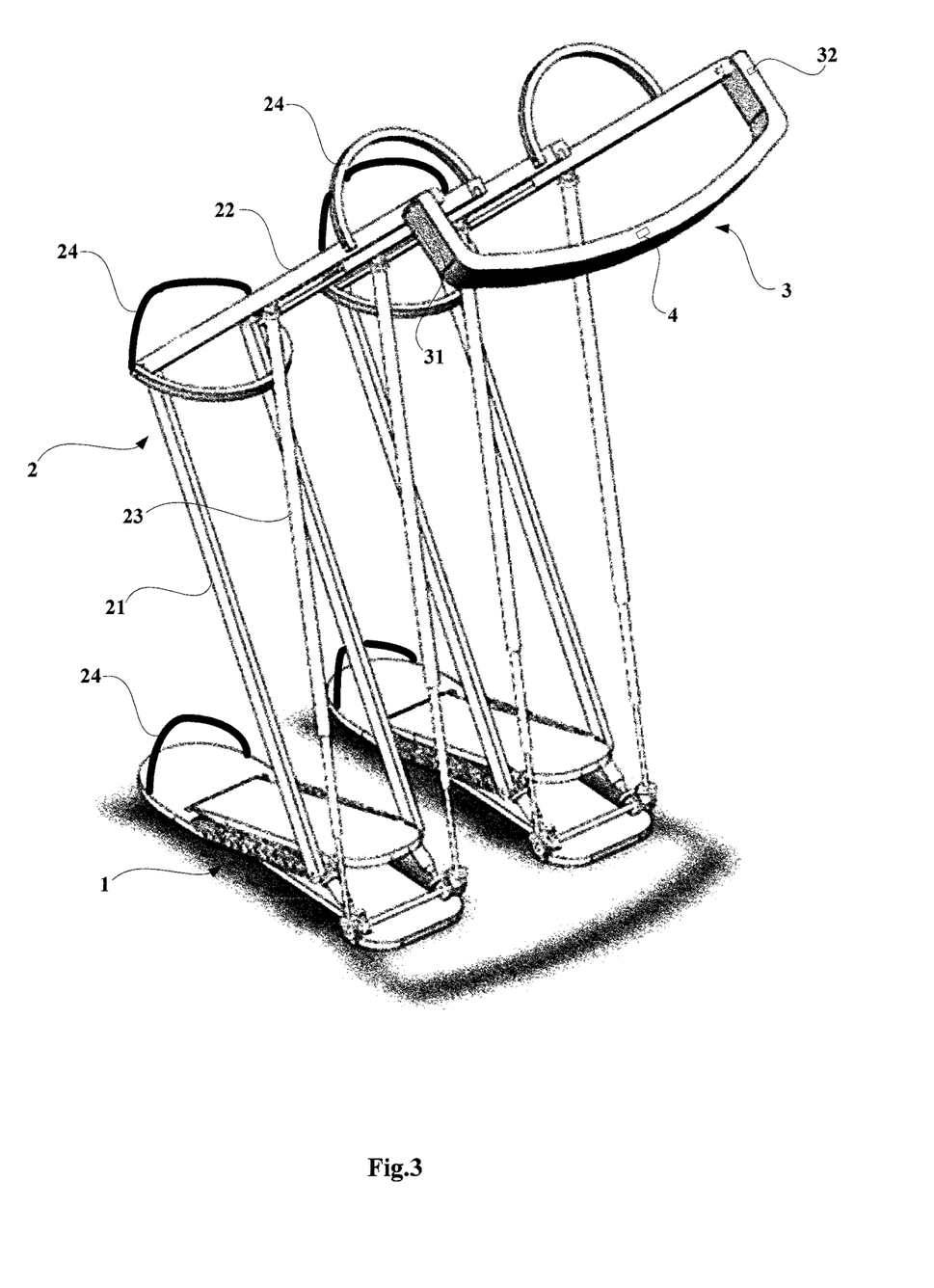
FIG. 3 illustrates a schematic view of a mechanical exoskeleton wearable apparatus according to another exemplary embodiment of the disclosure.

As illustrated in FIG. 3, in an exemplary embodiment of the disclosure, the mechanical exoskeleton wearable apparatus further comprises a first controller 4 which electrically connects with the first stroke regulators 23 and is configured to control the first stroke regulators 23 to be locked at the extending or retracting condition thereof once an extending or retraction stroke of the first stroke regulators 23 reaches a predetermined extending or retraction stroke threshold.

By this technical solution, the user may enable the seat functionality of the mechanical exoskeleton wearable apparatus by adjusting its posture. Specifically, e.g., the user may bend two legs downwards until the extending or retraction stroke of the first stroke regulators 23 reaches the predetermined extending or retraction stroke threshold; then, the first stroke regulators 23 are locked at the extending or retracting condition thereof, with a fixed angle between the shank supports 21 and the thigh supports 22, such that the user may sit safely on the hip support mechanism 3. The technical solution of the embodiment of the disclosure improves an intellectualization of the actions of the mechanical exoskeleton wearable apparatus, and enriches usable functionalities thereof. And the so-called extending or retraction stroke threshold may be determined empirically or by experiments, e.g., it may be preset as 20 cm.

In an embodiment of the disclosure, for example, the hip support mechanism and the thigh supports connect with each other fixedly, such that the hip support mechanism is located below the hip of the human body once both the shank supports and the thigh supports present respective postures which conform to a sitting posture of the human body.

By further reference to FIG. 3, in an embodiment of the disclosure, the hip support mechanism 3 is articulated with the thigh supports 22 and comprises a motor 31 configured to drive the hip support mechanism 3 in rotation relative to the thigh supports; and the first controller 4 further electrically connects with the motor 31 and is configured to control the motor 31 to drive the hip support mechanism 3 in rotation to a predetermined optimal supporting angle relative to the thigh supports 22 once the extending or retraction stroke of the first stroke regulators 23 reaches the predetermined extending or retraction stroke threshold.

The optimal supporting angle may be determined empirically or by experiments. With this technical solution, when the user walks or runs, the hip support mechanism 3 may be received at a waist of the user. For example, the hip mechanism 3 may rest against the waist by wrapping therearound from a rear portion thereof, so as to be received or accommodated there. When the seat functionality of the mechanical exoskeleton wearable apparatus is switched on, the hip support mechanism 3 may be adjusted automatically to an optimal supporting position so as to facilitate a more comfortable and safe sitting posture of the user.

Moreover, by way of example, the hip support mechanism 3 further comprises a vibrator 32; and the first controller 4 electrically connects with the vibrator 32 and is configured to control the vibrator 32 to vibrate once the hip support mechanism 3 is rotated to the predetermined optimal supporting angle relative to the thigh supports 22. When the hip support mechanism 3 completes an adjustment of its position, the vibrator 32 vibrates to prompt the user that it is safe to sit down. This solution further enhances safety when the seat functionality of the mechanical exoskeleton wearable apparatus is implemented by the prompt of vibration generated by the vibrator when the hip support mechanism 3 is in position.

By way of example, the first stroke regulator 23 is an air-cylinder type or a hydraulic-cylinder type stroke regulator. For example, it is in a form of an air-cylinder type stroke regulator, with a relatively light weight and thus is applicable to the mechanical exoskeleton wearable apparatus.

Figure 4:
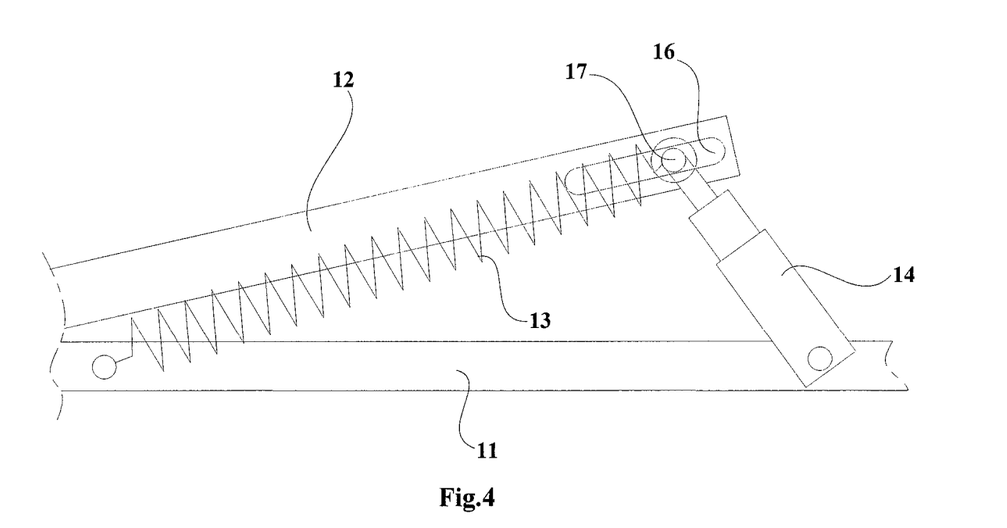
FIG. 4 illustrates a schematic view of a foot wearable mechanism according to an exemplary embodiment of the disclosure.
Figure 5:
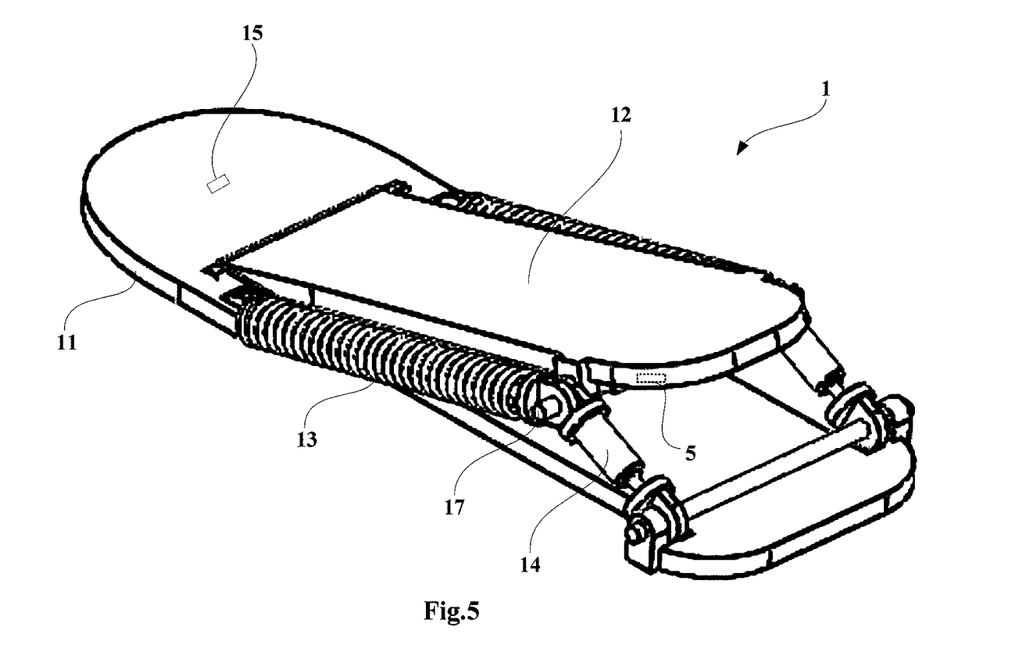
FIG. 5 illustrates a schematic view of a foot wearable mechanism in a lift-up condition of foot, according to an exemplary embodiment of the disclosure.
Figure 6:
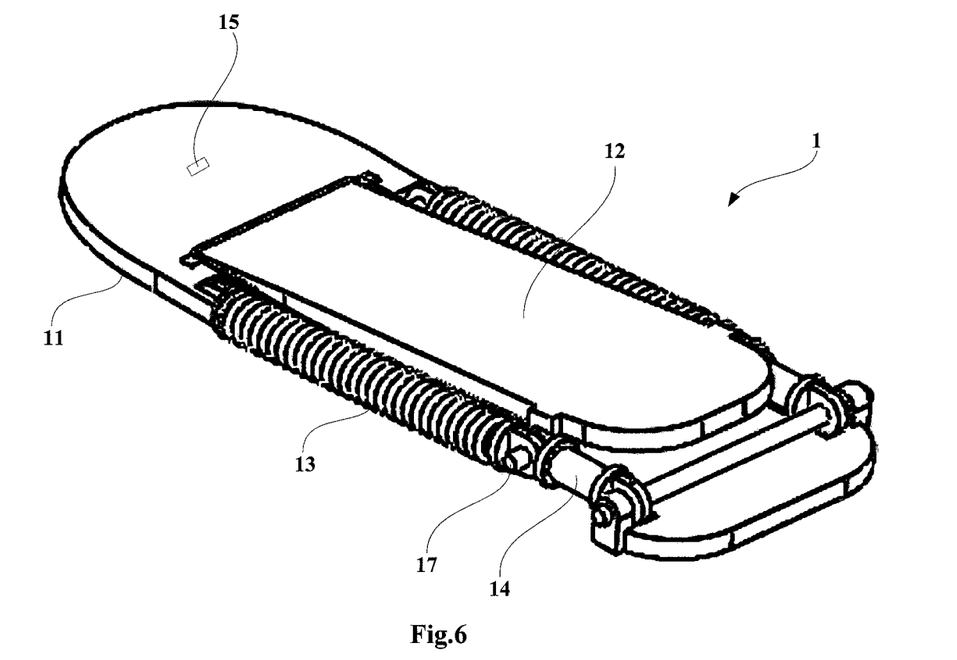
FIG. 6 illustrates a schematic view of a foot wearable mechanism in a step-down condition of foot, according to an exemplary embodiment of the disclosure.

As illustrated in FIGS. 4, 5 and 6, in an exemplary embodiment of the disclosure, the foot wearable mechanism comprises: a support 11; a liftable shoe-sole 12, a pair of springs 13, and a pair of second stroke regulators 14. A front end of the liftable shoe-sole 12 is articulated with the support 11, and each of two side portions of the liftable shoe-sole 12 which are located alongside the front end is provided with a corresponding one of a pair of chutes 16 in a lengthwise direction of the liftable shoe-sole respectively. Each spring and a corresponding one of the pair of second stroke regulators 14 are articulated with each other at one end thereof by a corresponding first articulated shaft 17 assembled slidably within a corresponding one of the pair of chutes 16 at respective side, and are articulated respectively with the support 11 at the other end facing away from the corresponding first articulated shaft 17, thereby an extending or retracting condition of the second stroke regulators 14 may be locked.

In a case that the user wears the mechanical exoskeleton wearable apparatus provided by an embodiment of the disclosure, the user may pivot the second stroke regulators 14 at a hinge joint with the support 11 around the support 11, e.g., in a clockwise direction, by adjusting and locking a length of extending or retraction of the second stroke regulators 14, such that a rear portion of the liftable shoe-sole 12 is lifted upwards and backwards at the end of the second stroke regulators 14 within the corresponding one of the pair of chutes 16. At that time, the foot wearable mechanism 1 is provided a damping/cushioning functionality which may alleviate a fatigue of the user in a movement significantly. Specifically, hereinafter, when the user' feet step down, the springs 13 are compressed, providing damping/cushioning for the feet of the user, especially for the sole of the feet; subsequently, when the user's feet lift up, the springs 13 return so as to jack up the corresponding first articulated shaft again, hereby lifting up the liftable shoe sole 12 again.

In an optional embodiment of the disclosure, by way of example, each of the second stroke regulators 14 is an electric cylinder provided with a switch; or otherwise is a lead-screw nut mechanism, for example. The user is capable of adjusting the extending or retracting condition and a locking condition of the second stroke regulators 14 manually.

In an exemplary embodiment as illustrated in FIG. 5, the foot wearable mechanism further comprises an acceleration sensor 15 and a second controller 5. The acceleration sensor 15 is provided on the support 11, and the second controller 5 electrically connects with the acceleration sensor 15 and the second stroke regulators 14 and controls the second stroke regulators 14 to extend so as to jack up the first articulated shafts 17 respectively once a walking speed of the user is larger than a predetermined walking speed threshold.

Specifically, in a case that the user wears the mechanical exoskeleton wearable apparatus provided by an embodiment of the disclosure, when the walking speed of the user is larger than the predetermined walking speed threshold, the foot wearable mechanism 1 switches on the damping/cushioning functionality automatically and intelligently so as to extend the second stroke regulators 14 to jack up the first articulated shafts 17 respectively, then the liftable shoe-sole is lifted up. As illustrated in FIG. 5, once the damping/cushioning functionality of the foot wearable mechanism 1 is switched on, the fatigue of the user in a movement may be alleviated significantly. The springs 13 are compressed even if the user's feet have not landed completely, and the foot wearable mechanism 1 may provide damping/cushioning for the feet of the user, and the foot wearable mechanism 1 in a step-down condition is illustrated in FIG. 6. The springs 13 return when the user's feet lift up, so as to jack up the first articulated shaft 17 and the liftable shoe-sole 12 once again. The walking speed threshold may be determined empirically or by experiments, e.g., it may be preset as a value of 1.5 m/s, and in a case such value is exceeded by a practical walking speed, it is considered that the user is running, then then damping/cushioning functionality of the foot wearable mechanism 1 is switched on.

In the embodiment, the specific type of the second stroke regulators 14 are not restricted, e.g., comprising but not limited to air-cylinder type stroke regulators, hydraulic-cylinder type stroke regulators, or lead-screw type stroke regulators.

Figure 7:
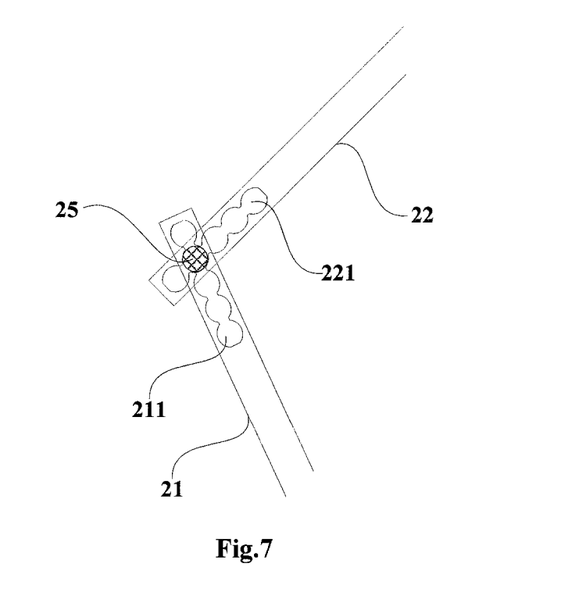
FIG. 7 illustrates a schematic view of an articulation between a shank support and a thigh support according to an exemplary embodiment of the disclosure.

As illustrated in FIG. 7, in an exemplary embodiment of the disclosure, the shank supports 21 and the thigh supports 22 are articulated with each other respectively by the second articulated shafts 25. Each of the thigh supports 22 has a plurality of first adjustment clamping slots 221 arranged in a length direction thereof, within any one of which a corresponding one of the second articulated shafts 25 is pivotably assembled. Each of the shank supports 21 has a plurality of second adjustment clamping slots 211 arranged in a length direction thereof, within which a corresponding one of the second articulated shafts 25 is pivotably assembled.

By above design, respective lengths of the thigh supports 22 and the shank supports 21 may be adjusted by assembling each second articulated shaft selectively into corresponding one of the first adjustment clamping slots 221 and one of the second adjustment clamping slots 211, such that the mechanical exoskeleton wearable apparatus may be applicable to users having different heights and leg lengths, i.e., having a relative wide applicable scope. The first adjustment clamping slots 221 and the second adjustment clamping slots 211 are elastic clamping slots, for example. As such, the second articulated shafts 25 is displaceable to an adjacent clamping slot and then snap fits therein resiliently by pulling/wrenching the second articulated shafts 25 forcibly. In other embodiments of the disclosure, for example, the clamping slots may be provided on either the thigh supports or the shank supports.

As illustrated in FIG. 3, in an embodiment, the shank supports 21, the thigh supports 22 and the first stroke regulators 23 of the leg wearable mechanism 2 are divided equally into two groups which are arranged symmetrically at both sides of a leg of the user, e.g., both inner side and outer side of each of the left and right legs. And the springs 13 and the second stroke regulators 14 of the foot wearable mechanism 1 are also divided equally into two groups which are arranged symmetrically at both sides of the liftable shoe-sole 12, i.e., both inner side and outer side of each liftable shoe-sole 12. With the design, both sides of each leg and each foot of the user are in a force-balanced condition, resulting in improvements of both the wearing comfort and the damping/cushioning functionality, and an improved reliability of the seat functionality.

Figure 8:
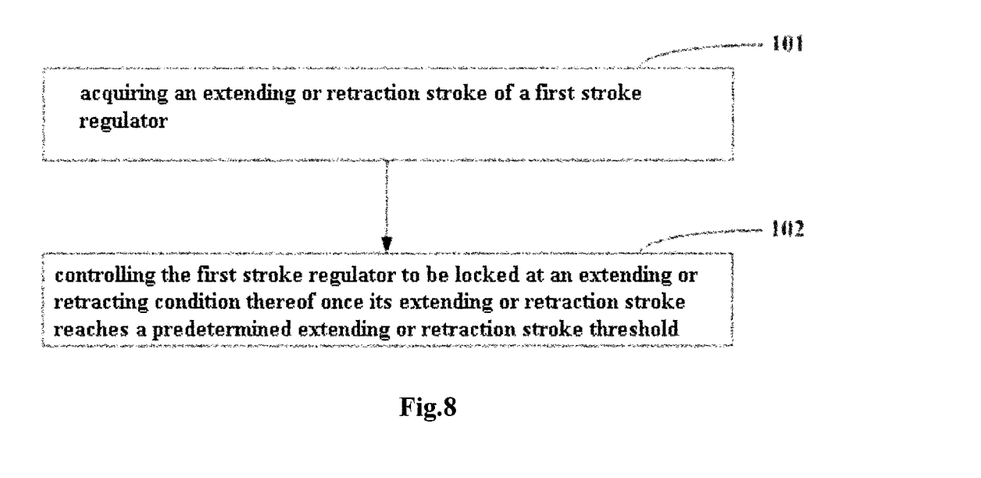
FIG. 8 illustrates a flow chart of an operation control method for a mechanical exoskeleton wearable apparatus according to an exemplary embodiment of the disclosure.

As illustrated in FIG. 8, on a basis of a similar inventive concept of the present disclosure, an operation control method for a mechanical exoskeleton wearable apparatus is provided by an embodiment of the disclosure, comprising following steps:

Step 101, acquiring an extending or retraction stroke of a first stroke regulator; and Step 102, controlling the first stroke regulator to be locked at an extending or retracting condition thereof once the extending or retraction stroke thereof reaches a predetermined extending or retraction stroke threshold.

With the operation control method of above embodiment of the disclosure, the mechanical exoskeleton wearable apparatus has a seat functionality which may be switched on automatically, so as to improve an intellectualization of the actions of the mechanical exoskeleton wearable apparatus, and to enrich usable functionalities thereof.

By way of example, the operation control method further comprises: controlling a motor to drive a hip support mechanism in rotation to a predetermined optimal supporting angle relative to a thigh support once the extending or retraction stroke of the first stroke regulator reaches the predetermined extending or retraction stroke threshold.

With the operation control method of the embodiment of the disclosure, when the seat functionality of the mechanical exoskeleton wearable apparatus is switched on, the hip support mechanism is at an optimal supporting position, so as to facilitate a more comfortable and safe sitting posture of the user.

In a further embodiment of the disclosure, the operation control method further comprises: controlling a vibrator to vibrate once the hip support mechanism is rotated to the predetermined optimal supporting angle relative to the thigh support.

With the operation control method of the embodiment of the disclosure, when the hip support mechanism 3 completes an adjustment of its position, the vibrator vibrates to prompt the user that it is safe to sit down. This solution further enhances safety when the seat functionality of the mechanical exoskeleton wearable apparatus is implemented.

By way of example, the operation control method further comprises:

acquiring a walking speed of a user a user who wears the mechanical exoskeleton wearable apparatus; and controlling the second stroke regulator to extend so as to jack up a corresponding articulated shaft articulated between a spring and itself once the walking speed of the user is larger than a predetermined walking speed threshold.

With the operation control method of the embodiment of the disclosure, when the walking speed of the user is larger than the predetermined walking speed threshold, the foot wearable mechanism has a damping/cushioning functionality which may alleviate a fatigue of the user in a movement significantly.

Figure 9:
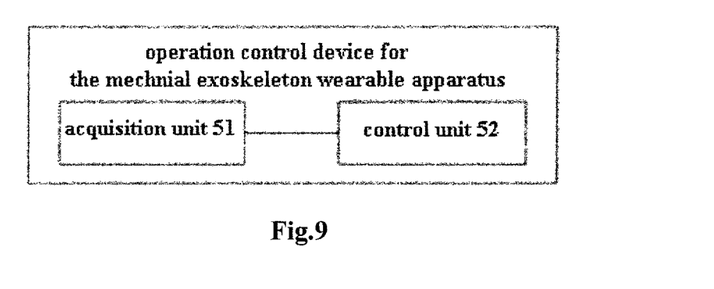
FIG. 9 illustrates a schematic view of an operation control device for a mechanical exoskeleton wearable apparatus according to another exemplary embodiment of the disclosure.

As illustrated in FIG. 9, on a basis of a similar inventive concept of the present disclosure, an operation control device for a mechanical exoskeleton wearable apparatus is provided by an embodiment of the disclosure, comprising:

an acquisition unit 51 configured to acquire an extending or retraction stroke of a first stroke regulator; and a control unit 52 configured to control the first stroke regulator to be locked at an extending or retracting condition thereof once the extending or retraction stroke thereof reaches a predetermined extending or retraction stroke threshold.

With the operation control device of above embodiment of the disclosure, the mechanical exoskeleton wearable apparatus has a seat functionality which may be switched on automatically, so as to improve an intellectualization of the actions of the mechanical exoskeleton wearable apparatus, and to enrich usable functionalities thereof.

By way of example, the control unit 52 is further configured to control a motor to drive a hip support mechanism in rotation to a predetermined optimal supporting angle relative to a thigh support once the extending or retraction stroke of the first stroke regulator reaches the predetermined extending or retraction stroke threshold.

With the operation control device of the embodiment of the disclosure, when the seat functionality of the mechanical exoskeleton wearable apparatus is switched on, the hip support mechanism is at an optimal supporting position, so as to facilitate a more comfortable and safe sitting posture of the user.

In a further embodiment of the disclosure, the control unit 52 is further configured to control a vibrator to vibrate once the hip support mechanism is rotated to the predetermined optimal supporting angle relative to the thigh support.

With the operation control device of the embodiment of the disclosure, when the hip support mechanism 3 completes an adjustment of its position, the vibrator vibrates to prompt the user that it is safe to sit down. This solution further enhances safety when the seat functionality of the mechanical exoskeleton wearable apparatus is implemented.

By way of example, the acquisition unit 51 is further configured to acquire a walking speed of a user who wears the mechanical exoskeleton wearable apparatus; and the control unit 52 is further configured to control the second stroke regulator to extend so as to jack up a corresponding articulated shaft articulated between a spring and itself once the walking speed of the user is larger than a predetermined walking speed threshold.

With the operation control device of the embodiment of the disclosure, when the walking speed of the user is larger than the predetermined walking speed threshold, the foot wearable mechanism has a damping/cushioning functionality which may alleviate a fatigue of the user in a movement significantly.

According to an embodiment of the disclosure, by way of example, the acquisition unit 51 comprises an IMU (Inertial Measurement Unit) and/or a 6-axis navigation combination of accelerometer and gyroscope, either being configured to acquire the walking speed of the user who wears the mechanical exoskeleton wearable apparatus and/or the extending or retraction stroke of a first stroke regulator.

According to an embodiment of the disclosure, by way of example, the control unit 52 is configured to be coupled to the motor and/or the vibrator to implement an operation control thereon, so as to:
  control the first stroke regulator to be locked at an extending or retracting condition thereof once the extending or retraction stroke thereof reaches a predetermined extending or retraction stroke threshold;
  control the motor to drive a hip support mechanism in rotation to a predetermined optimal supporting angle relative to a thigh support once the extending or retraction stroke of the first stroke regulator reaches the predetermined extending or retraction stroke threshold;
  control the vibrator to vibrate once the hip support mechanism is rotated to the predetermined optimal supporting angle relative to the thigh support;
  control the second stroke regulator to extend so as to jack up a corresponding articulated shaft articulated between a spring and itself once the walking speed of the user is larger than a predetermined walking speed threshold; and
  realize any combination of above four aspects.

By way of example, the control unit 52 comprises:
  a controller such as a STM32 serial microcontroller and the like, configured to produce a PWM wave so as to implement a duty cycle control on the motor, and/or a signal to control the switch-on and switch-off of the vibrator; and
  an encoder, e.g., a rotary encoder installed on the motor and configured to read PWM wave and to perform conversion to generate a control command.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although the disclosure is described in view of the attached drawings, the embodiments disclosed in the drawings are only intended to illustrate the preferable embodiment of the present disclosure exemplarily, and should not be deemed as a restriction thereof.

Although several exemplary embodiments of the general concept of the present disclosure have been shown and described, it would be appreciated by those skilled in the art that various changes or modifications may be made in these embodiments without departing from the principles and spirit of the disclosure and lie within the scope of present application, which scope is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A mechanical exoskeleton wearable apparatus, comprising:
   a foot wearable mechanism;
   a leg wearable mechanism comprising:
     shank supports articulated with the foot wearable mechanism, thigh supports articulated with the shank supports, and first stroke regulators articulated at both ends with the foot wearable mechanism and the thigh supports respectively; and
   a hip support mechanism configured to connect with the thigh supports,
   wherein each of the first stroke regulators is configured to be extendable and retractable with a leg action of a user who wears the mechanical exoskeleton wearable apparatus, and an extending or retracting condition thereof is lockable;
   wherein each of the first stroke regulators is an electric cylinder provided with a switch; or
   wherein each of the first stroke regulator comprises:
   a lock-pin, and
   a first adjustment rod and a second adjustment rod which are assembled slidably relative to each other and provided respectively with a plurality of pinholes arranged in a relative sliding direction, the extending or retracting condition thereof being locked once the lock-pin is inserted into a pair of respective pinholes of the first adjustment rod and the second adjustment rod disposed to be aligned with each other.

2. The mechanical exoskeleton wearable apparatus according to claim 1, further comprising a first controller which electrically connects with the first stroke regulators and is configured to control the first stroke regulators to be locked at the extending or retracting condition thereof once an extending or retraction stroke of the first stroke regulators reaches a predetermined extending or retraction stroke threshold.

3. The mechanical exoskeleton wearable apparatus according to claim 2, wherein the hip support mechanism is articulated with the thigh supports and comprises a motor configured to drive the hip support mechanism in rotation relative to the thigh supports; and
wherein the first controller electrically connects with the motor and is configured to control the motor to drive the hip support mechanism in rotation to a predetermined optimal supporting angle relative to the thigh supports once the extending or retraction stroke of the first stroke regulators reaches the predetermined extending or retraction stroke threshold.

4. The mechanical exoskeleton wearable apparatus according to claim 3, wherein the hip support mechanism further comprises a vibrator; and
wherein the first controller electrically connects with the vibrator and is configured to control the vibrator to vibrate once the hip support mechanism is rotated to the predetermined optimal supporting angle relative to the thigh supports.

5. The mechanical exoskeleton wearable apparatus according to claim 1, wherein the foot wearable mechanism comprises:
a support;
a liftable shoe-sole, a front end thereof being articulated with the support, and each of two side portions thereof which are located alongside the front end being provided with a corresponding one of a pair of chutes in a lengthwise direction of the liftable shoe-sole respectively;
a pair of second stroke regulators; and
a pair of springs, each spring and a corresponding one of the pair of second stroke regulators being articulated with each other at one end thereof by a corresponding first articulated shaft assembled slidably within a corresponding one of the pair of chutes at respective side, and being articulated respectively with the support at the other end facing away from the corresponding first articulated shaft, such that an extending or retracting condition of the second stroke regulators is lockable.

6. The mechanical exoskeleton wearable apparatus according to claim 5, wherein each of the second stroke regulators comprises:
an electric cylinder provided with a switch, or
a lead-screw nut.

7. The mechanical exoskeleton wearable apparatus according to claim 5, wherein the foot wearable mechanism further comprises:
an acceleration sensor provided on the support; and
a second controller, which electrically connects with the acceleration sensor and the second stroke regulators and is configured to control each of the second stroke regulators to extend so as to jack up the corresponding first articulated shaft once a walking speed of the user is larger than a predetermined walking speed threshold.

8. The mechanical exoskeleton wearable apparatus according to claim 5, wherein the shank supports, the thigh supports and the first stroke regulators of the leg wearable mechanism are divided equally into two groups which are arranged symmetrically at both sides of a leg of the user; and
wherein the springs and the second stroke regulators of the foot wearable mechanism are divided equally into two groups which are arranged symmetrically at both sides of the liftable shoe-sole.

9. The mechanical exoskeleton wearable apparatus according to claim 1, wherein the shank supports and the thigh supports are articulated with each other by second articulated shafts, respectively; and
wherein each of the thigh supports has a plurality of first adjustment clamping slots arranged in a length direction thereof, within any one of which a corresponding one of the second articulated shafts is pivotably assembled; and/or
wherein each of the shank supports has a plurality of second adjustment clamping slots arranged in a length direction thereof, within any one of which a corresponding one of the second articulated shafts is pivotably assembled.

10. The mechanical exoskeleton wearable apparatus according to claim 1, wherein the hip support mechanism is in a form of U-shape.

11. The mechanical exoskeleton wearable apparatus according to claim 10, wherein each of the foot wearable mechanism and the leg wearable mechanism is provided with a binding band, respectively.

12. An operation control method for a mechanical exoskeleton wearable apparatus, wherein the mechanical exoskeleton wearable apparatus comprises:
a foot wearable mechanism;
a leg wearable mechanism comprising:
shank supports articulated with the foot wearable mechanism, thigh supports articulated with the shank supports, and first stroke regulators articulated at both ends with the foot wearable mechanism and the thigh supports respectively; and
a hip support mechanism configured to connect with the thigh supports,
wherein each of the first stroke regulators is configured to be extendable and retractable with a leg action of a user who wears the mechanical exoskeleton wearable apparatus, and an extending or retracting condition thereof is lockable,
wherein the operation control method comprises:
acquiring an extending or retraction stroke of the first stroke regulator; and
controlling the first stroke regulator to be locked at an extending or retracting condition thereof once the extending or retraction stroke thereof reaches a predetermined extending or retraction stroke threshold;
wherein each of the first stroke regulators is an electric cylinder provided with a switch; or
wherein each of the first stroke regulator comprises:
a lock-pin, and
a first adjustment rod and a second adjustment rod which are assembled slidably relative to each other and provided respectively with a plurality of pinholes arranged in a relative sliding direction, the extending or retracting condition thereof being locked once the lock-pin is inserted into a pair of respective pinholes of the first adjustment rod and the second adjustment rod disposed to be aligned with each other.

13. The operation control method according to claim 12, further comprising:
controlling a motor to drive a hip support mechanism in rotation to a predetermined optimal supporting angle relative to a thigh support once the extending or retraction stroke of the first stroke regulator reaches the predetermined extending or retraction stroke threshold.

14. The operation control method according to claim 13, further comprising:

controlling a vibrator to vibrate once the hip support mechanism is rotated to the predetermined optimal supporting angle relative to the thigh support.

15. The operation control method according to claim 12, further comprising:
acquiring a walking speed of a user who wears the mechanical exoskeleton wearable apparatus; and
controlling the second stroke regulator to extend so as to jack up a corresponding articulated shaft articulated between a spring and itself once the walking speed of the user is larger than a predetermined walking speed threshold.

16. An operation control device for a mechanical exoskeleton wearable apparatus, wherein the mechanical exoskeleton wearable apparatus comprises:
a foot wearable mechanism;
a leg wearable mechanism comprising:
shank supports articulated with the foot wearable mechanism, thigh supports articulated with the shank supports, and first stroke regulators articulated at both ends with the foot wearable mechanism and the thigh supports respectively; and
a hip support mechanism configured to connect with the thigh supports,
wherein each of the first stroke regulators is configured to be extendable and retractable with a leg action of a user who wears the mechanical exoskeleton wearable apparatus, and an extending or retracting condition thereof is lockable,
wherein the operation control device comprises:
an acquisition unit configured to acquire an extending or retraction stroke of the first stroke regulator; and
a control unit configured to control the first stroke regulator to be locked at an extending or retracting condition thereof once the extending or retraction stroke thereof reaches a predetermined extending or retraction stroke threshold;
wherein each of the first stroke regulators is an electric cylinder provided with a switch; or
wherein each of the first stroke regulator comprises:
a lock-pin, and
a first adjustment rod and a second adjustment rod which are assembled slidably relative to each other and provided respectively with a plurality of pinholes arranged in a relative sliding direction, the extending or retracting condition thereof being locked once the lock-pin is inserted into a pair of respective pinholes of the first adjustment rod and the second adjustment rod disposed to be aligned with each other.

17. The operation control device according to claim 16, wherein
the control unit is further configured to control a motor to drive a hip support mechanism in rotation to a predetermined optimal supporting angle relative to a thigh support once the extending or retraction stroke of the first stroke regulator reaches the predetermined extending or retraction stroke threshold.

18. The operation control device according to claim 17, wherein
the control unit is further configured to control a vibrator to vibrate once the hip support mechanism is rotated to the predetermined optimal supporting angle relative to the thigh support.

19. The operation control device according to claim 16, wherein
the acquisition unit is further configured to acquire a walking speed of a user who wears the mechanical exoskeleton wearable apparatus; and
the control unit is further configured to control the second stroke regulator to extend so as to jack up a corresponding articulated shaft articulated between a spring and itself once the walking speed of the user is larger than a predetermined walking speed threshold.

* * * * *